United States Patent
Lu et al.

(10) Patent No.: US 9,809,546 B2
(45) Date of Patent: Nov. 7, 2017

(54) PROCESS FOR PRODUCING DIAMINE DERIVATIVE

(71) Applicant: CHUNGHWA CHEMICAL SYNTHESIS & BIOTECH CO. LTD., New Taipei (TW)

(72) Inventors: Tzu-Chiang Lu, New Taipei (TW); Chien-Yi Chen, New Taipei (TW); Ching-Shuen Cheng, New Taipei (TW); Chin-Cheng Mai, New Taipei (TW)

(73) Assignee: Chungwha Chemical Synthesis & Biotech Co., Ltd., New Taipei (TW)

( * ) Notice: Subject to any disclaimer, the term of this patent is extended or adjusted under 35 U.S.C. 154(b) by 27 days.

(21) Appl. No.: 15/153,352

(22) Filed: May 12, 2016

(65) Prior Publication Data
US 2017/0260138 A1 Sep. 14, 2017

(30) Foreign Application Priority Data
Mar. 14, 2016 (TW) .............................. 105107737 A

(51) Int. Cl.
*C07D 213/75* (2006.01)
(52) U.S. Cl.
CPC ................................. *C07D 213/75* (2013.01)
(58) Field of Classification Search
CPC .................................................. C07D 213/75
See application file for complete search history.

(56) References Cited

U.S. PATENT DOCUMENTS

| 7,365,205 B2 | 4/2008 | Ohta et al. |
| 8,357,808 B2 | 1/2013 | Koyama et al. |
| 8,686,189 B2 | 4/2014 | Sato et al. |

FOREIGN PATENT DOCUMENTS

| WO | WO-03/000657 | 1/2003 |
| WO | WO-2007/032498 | 3/2007 |
| WO | WO-2010/104078 | 9/2010 |

OTHER PUBLICATIONS

OChemPal. "Secondary Amine." © 2016. Available from: < http://www.ochempal.org/index.php/alphabetical/s-t/secondary-amine/>.*

* cited by examiner

*Primary Examiner* — Noble Jarrell
*Assistant Examiner* — John S Kenyon
(74) *Attorney, Agent, or Firm* — Muncy, Geissler, Olds & Lowe, P.C.

(57) ABSTRACT

The present invention provides a low-toxic and high-recovery industrial process for synthesizing an optically active diamine derivative represented by formula (D), the process comprising the steps of: (a) mixing a compound represented by formula (A) and a compound represented by formula (C) in organic solvents and secondary amine; (b) reaction under heating; (c) cooling and adding water to the mixed solution, allowing it to crystallize to obtain the compound represented by formula (D).

9 Claims, No Drawings

PROCESS FOR PRODUCING DIAMINE DERIVATIVE

BACKGROUND OF THE INVENTION

1. Technical Field

The present invention provides a process for synthesizing a compound of the following Formula (D), which is an important intermediate for manufacturing activated blood coagulation factor Xa (FXa) inhibitor, Edoxaban. The said process is simple and can be used as an industrial process

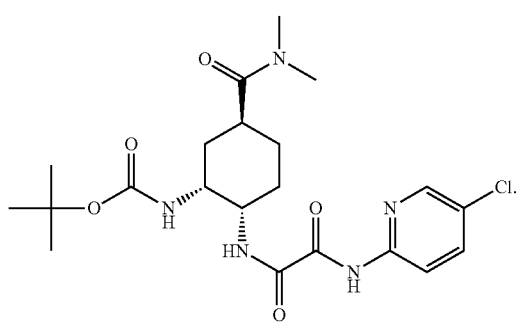
(D)

2. Description of Related Art

Activated blood coagulation factor Xa (FXa) inhibitor, Edoxaban, can block harmful effects and be used as an effective compound for preventing and/or treating thromboembolism, which is a compound of the following Formula (1), $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide:

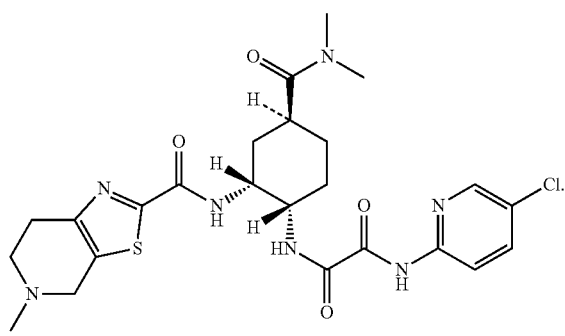
(1)

The compound of the following formula (D), tert-butyl (1R,2S,5S)-2-({2-[(5-chloropyridin-2-yl)amino]-2-oxoacetyl}amino)-5-(dimethylaminocarbonyl)cyclohexylcarbamate, is a known intermediate compound for manufacturing the compound of Formula (1). PCT laid-open patent application no. WO 2003/000657 (also published as JP2001-187105A and U.S. Pat. No. 7,365,205B2) disclosed a process for synthesizing compound of Formula (D), which comprises: treating a compound of the following formula (C), ethyl 2-[(5-chloropyridin-2-yl)amino]-2-oxoacetate monohydrochloride, from its ethyl ester to obtain lithium compound;

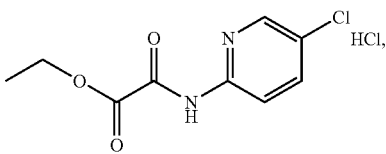
(C)

added a compound represented by the following formula (A) as tert-butyl {(1R,2S,5S)-2-amino-5-[(dimethylamino)carbonyl]cyclohexyl}carbamate, hydroxybenzotriazole monohydrate, and 1-ethyl-3-(3-dimethylaminopropyl)carbodiimide hydrochloride to the mixture of the lithium compound in dichloromethane and reacted; and then purified by column chromatography on silica gel to obtain the compound of Formula (D)

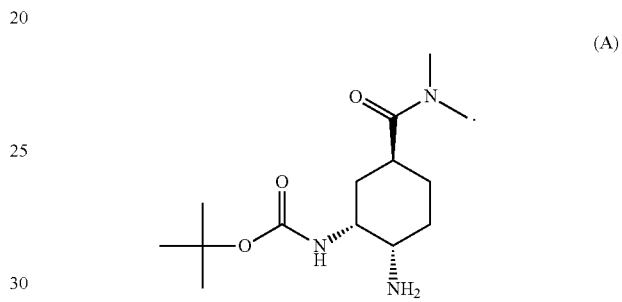
(A)

PCT laid-open patent application no. WO 2007/032498 (also published as JP2007-106759A and U.S. Pat. No. 8,686,189B2) disclosed a process for synthesizing the compound of formula (D), which comprises: adding the oxalate of compound of formula (A) into excessive amount of tertiary amines for neutralizing the salt of thereof; and then adding the compound of formula (C) to the mixture.

PCT laid-open patent application no. WO 2010/104078 (also published as U.S. Pat. No. 8,357,808B2) claims a similar process to the above patents, characterized in treating the compound of formula (C) with tertiary amines in $C_2$-$C_4$ nitriles solvent and then adding the oxalate of compound of formula (A) to the mixture.

BRIEF SUMMARY OF THE INVENTION

The inventor of the present invention has investigated the industrial process of synthesizing the compound of formula (D). The inventor found that the process of PCT laid-open patent application no. WO 2003/000657 has to treat ethyl ester of the compound of formula (C) to obtain lithium compound; then added compound of formula (A), hydroxybenzotriazole monohydrate, and 1-ethyl-3-(3-dimethylaminopropyl)carbodiimide hydrochloride to the mixture of the lithium compound in dichloromethane and reacted; and purified by column chromatography on silica gel to obtain the compound of formula (D). This is a lengthy, complicated, high cost, and low recovery process. As for the process disclosed in PCT laid-open patent application no. WO 2007/032498, the compound of formula (A) would turn into colloid which may cause the reaction system hardened and make the agitation very difficult; further, it leads to increase the amount of by-products in the reaction system and drastically decrease the recovery of the compound of formula (D). Due to the fact that avoidance of hardening effect is difficult, it is not a proper industrial process.

Although PCT laid-open patent application no. WO 2010/104078 disclosed the process that solved the problem of PCT laid-open patent application no. WO 2007/032498, by decreasing the amount of the by-products and avoiding the recovery of the compound of formula (D) decreasing drastically. It still exist the problem of hardening effect, leading to uneven agitation during scaling up the production of the compound of formula (D) and having difficulty in manipulation, causing the compound of formula (D) low recovery. Moreover, the process uses highly toxic solvent of nitriles, which may easy to damage the environment and human healthy. Therefore, it is an urgent priority avoiding the production of by-products and decreasing the effect of hardening, for stabilizing the process with high recovery of the compound of formula (D), furthermore, decreasing the damage to the environment and human healthy.

In order to solve these problems, the inventor of the present invention has devoted to investigate the solution. Surprisingly, the inventors found out that by adding excessive amount of secondary amine to the compound of formula (C) with non-nitriles organic solvent, and adding the compound of formula (A) for heating, which is a simple way appropriate for industrial use, solving the problems of the hardening effect, manipulation difficulties, and decreasing the damage to the environment and human healthy; therefore, stabilizing the quality of high recovery of the compound of formula (D) for production.

The benefit of the present invention is to provide an industrial process not only solving the problems of the hardening effect, manipulation difficulties, and decreasing the damage to the environment and human healthy but also stabilizing the quality of high recovery of the formula of compound (D) for production.

One aspect of the present invention is to provide a process for producing a compound of formula (D):

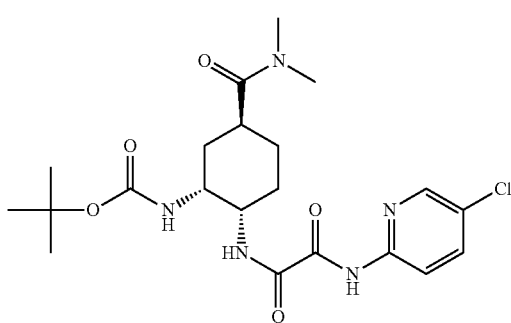

(D)

comprising the following steps:
step 1: adding a compound of formula (C) into an organic solvent and treating with a secondary amine:

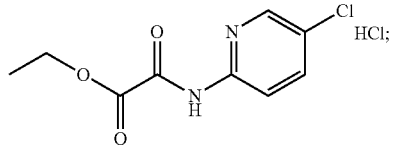

(C)

step 2: adding a compound of formula (A) or a salt or a salt hydrate thereof into the mixture of step 1:

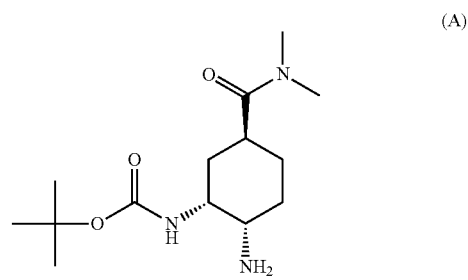 [SMILES: CN(C)C(=O)[C@H]1CC[C@H](N)[C@H](NC(=O)OC(C)(C)C)C1]

(A)

and
step 3: crystallizing the mixture processed in step 2.

In a preferable embodiment, the organic solvent contains dimethyl sulfoxide, dimethylformamide, or a component solvent of thereof.

In a preferable embodiment, the compound of formula (C) is added in an amount of 1.1 to 1.5 molar equivalents with respect to the compound of formula (A).

In a preferable embodiment, the secondary amine comprises one or more selected from the group consisting of di($C_1$-$C_4$ alkyl)amines.

In a preferable embodiment, the secondary amine comprises diethylamine, dipropylamine, dibutylamine, diisopropylamine or diisobutylamine.

In a preferable embodiment, the step 1 includes adding the compound of formula (C) into the organic solvent first, and then adding the secondary amine.

In a preferable embodiment, the Step 1 includes adding the secondary amine into the organic solvent first, and then adding the compound of formula (C).

In a preferable embodiment, the said adding of the compound of formula (C) or of the secondary amine is performed at a temperature in the range of 19° C. to 65° C.

In a preferable embodiment, the Step 1, the secondary amine is added in an amount of 1.5 to 5.5 molar equivalents with respect to the compound of formula (C).

In a preferable embodiment, the Step 2 includes agitating the mixture at a temperature in the range of 60° C. to 95° C.

In a preferable embodiment, a duration for said agitating ranges between 4 hours to 24 hours.

The compound of formula (D) of the present invention is an intermediate compound for manufacturing the compound of formula (1-1):

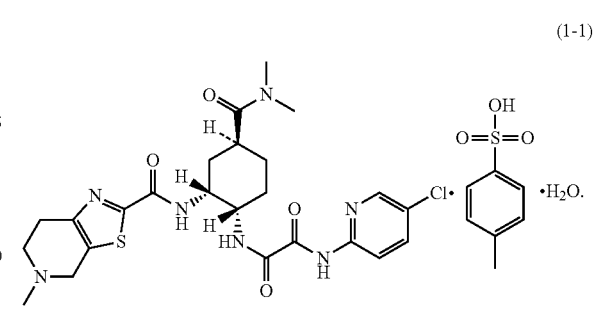

(1-1)

Therefore, another aspect of the present invention is a process of manufacturing compound of formula (1-1), which includes the process of synthesizing the compound of formula (D).

In a preferable embodiment, the process of manufacturing compound of formula (1-1) includes using the process of the first aspect of the present invention to synthesize compound of formula (D), and further includes: removing the tert-butoxycarbonyl protecting group of compound of formula (D) to obtain compound of formula (E) or a salt thereof:

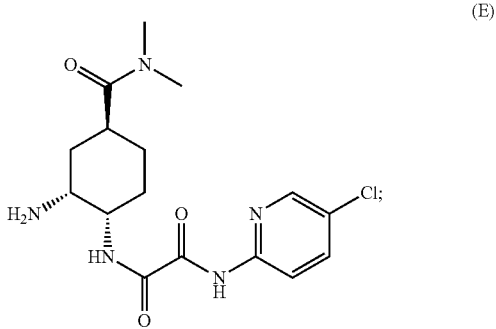 [SMILES: CN(C)C(=O)[C@H]1CC[C@H](NC(=O)C(=O)Nc2ccc(Cl)cn2)[C@H](N)C1]

(E)

condensing the compound of formula (E) with a compound of formula (B) to obtain the compound of formula (1):

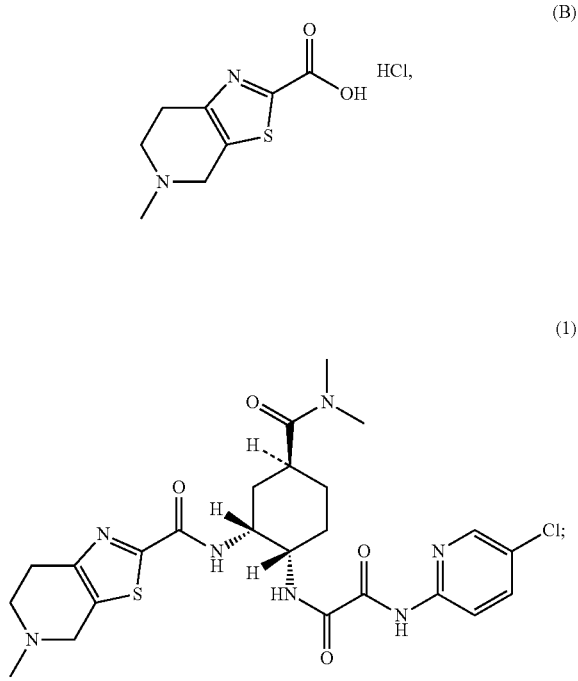

(B)

(1)

and
treating the compound of formula (1) with p-toluenesulfonic acid or a hydrate thereof to obtain the compound of formula (1-1).

DETAILED DESCRIPTION OF THE INVENTION

The present invention is to provide a process of synthesizing the compound of formula (D), the process includes: step1: placing a compound of formula (C) into an organic solvent to form a mixture and processing the mixture with a secondary amine; step2: adding a compound (A) or a salt thereof or a salt hydrate thereof into the mixture of Step1; and step3: crystallizing the mixture processed in step 2 to obtain compound of formula (D).

The orders in step1 have no particular limitation. For example, the secondary amine can be added after adding the compound (C) into the organic solvent, or before adding the compound (C). The amount of the secondary amine in step 1 is ranged from 1.5 molar equivalents to 5.5 molar equivalents with respect to the compound of formula (C), such as in the amount of molar equivalent of 1.5, 2.0, 2.5, 3.0, 3.5, 4.0, 4.5, 5.0, or 5.5. Furthermore, the secondary amine can be added all at once, or can be divided in to several times to add, but is preferred to be added all at once. The said secondary amine comprises one or more selected from the group consisting of di($C_1$-$C_4$ alkyl)amines, such as diethylamine, dipropylamine, dibutylamine, diisopropylamine or diisobutylamine, which can be used singly or as a mixture, preferably diisopropylamine.

The said adding of the secondary amine is preferably performed at a temperature ranging between 19° C. to 65° C., such as 20° C., 25° C., 30° C., 35° C., 40° C., 45° C., 50° C., 55° C., 60° C., or 65° C., more preferably at room temperature.

The said organic solvent in step 1 is preferably dimethyl sulfoxide, dimethylformamide, or a component solvent of thereof, more preferably dimethyl sulfoxide. The amount of the said organic solvent is not particularly limited, but more preferably ranged between 5 to 15 parts by volume (v/W), such as 6 to 8 parts by volume.

The amount of compound of formula (C) in step 2 is added in an amount ranging between 1.1 to 1.5 molar equivalents of the compound of formula (A), such as 1.1, 1.2, 1.3, 1.4, or 1.5 molar equivalents. The temperature of step 2 for agitating the mixture is performed at 60° C. to 95° C., such as 60° C., 70° C., 75° C., 80° C., 85° C., 90° C., or 95° C., preferably 68° C. The agitating time is above 4 hours, preferably 4 hour to 24 hour, more preferably 7 hour.

The crystallizing process in Step 3 is preferably to cool the mixture of step 2, and then adding water with agitation for crystallization. The cooling temperature has no particular limitation, such as −20° C. to 50° C., preferably −20° C. to 40° C., more preferably 0° C. to 30° C., and most preferably 25° C. In order to obtain the crystals, the preferable way is to collect the crystal by washing the crystals after the filtration, and then dried it. The drying method has no particular limitation, preferably using hot air drying, and the drying temperature ranges from 30° C. to 60° C., such as 30° C., 40° C., 50° C., or 60° C., preferably 50° C.

The compound of formula (D) made by the process of the present invention is the intermediate compound for manufacturing the compound of formula (1), and the process of manufacturing the compound of formula (1) has no particular limitation. The compound of formula (1) can be manufactured by any conventional way. The compound of formula (1) can be free form or a hydrate thereof, or medicinal acceptable salt or a hydrate thereof, such as hydrochloride, sulfate, phosphate, nitrate, benzoate, methanesulfonate, p-toluenesulfonate, acetate, propionate, oxalate, malonate, glutarate, adipate, tartrate, maleate, fumarate, etc., which is preferably p-toluenesulfonate, or a hydrate thereof.

The compound of formula (1) thus obtained exhibits a high inhibitory effect on activated blood coagulation factor X (FXa) and as such, is useful as an anticoagulant agent or a preventive and/or therapeutic agent for thrombus or embolism. The compound of formula (1) is useful as a pharmaceutical drug for mammals including humans, an activated blood coagulation factor Xa inhibitor, an anticoagulant agent, a preventive and/or therapeutic agent for thrombus or embolism, a preventive and/or therapeutic agent for thrombotic disease, for example, a preventive and/or therapeutic agent for cerebral infarction, cerebral embolism, myocardial infarction, angina pectoris, unstable angina, acute coronary syndrome (ACS), pulmonary infarction, pulmonary embolism, thromboembolism or seizure accompanying nonvalvular atrial fibrillation (NVAF), deep vein thrombosis, disseminated intravascular coagulation syndrome, thrombosis after prosthetic valve/joint replacement, thromboembolism after total hip replacement (THR), thrombosis and reocclusion after revascularization, thrombosis at the time of extracorporeal circulation, blood coagulation at the time of blood collection, Buerger's disease, thromboembolism accompanying systemic inflammatory response syndrome (SIRS), or thromboembolism accompanying multiple organ dysfunction syndrome (MODS), or a bulk pharmaceutical for these preventive and/or therapeutic agents.

The present invention can be further understood with the following definitions and exemplary embodiment. The follow description is the exemplary embodiment of the present invention disclosed in the much more detailed so that the concept of the present invention can be easily implemented by those skilled in the art of the present invention.

[Comparative Example] Synthesis of tert-butyl (1R, 2S,5S)-2-({2-[(5-chloropyridin-2-yl)amino]-2-oxoacetyl}amino)-5-(dimethylaminocarbonyl)cyclohexyl-carbamate As a start, 4.25 g of ethyl 2-[(5-chloropyridin-2-yl)amino]-2-oxoacetate monohydrochloride was weighted and suspended in 25 ml of acetonitrile. At 60±2° C., 7.5 g of triethylamine was added into the suspension first, and then 5 g of tert-butyl {(1R,2S,5S)-2-amino-5-[(dimethylamino)carbonyl]cyclohexylcarbamate oxalate monohydrate was added. The mixture was agitated for 7 hours at 65±1° C. The reaction solution was cooled to 25° C. Afterward, 125 ml of water was added and agitating was performed for 10 minutes. Crystals as products were collected by filtration, washed with water, and air-dried at 50° C. to yield 5.168 g of the title compound (with an equivalent recovery of 88%).

[Executive Example 1] Synthesis of tert-butyl (1R, 2S,5S)-2-({2-[(5-chloropyridin-2-yl)amino]-2-oxoacetyl}amino)-5-(dimethylaminocarbonyl)cyclohexyl-carbamate As a start, 2.02 g of ethyl 2-[(5-chloropyridin-2-yl)amino]-2-oxoacetate monohydrochloride was weighted and suspended in 15 ml of dimethyl sulfoxide. At the room temperature, 3.86 ml of diisopropylamine was added into the suspension first, and then 2.0 g of tert-butyl {(1R,2S,5S)-2-amino-5-[(dimethylamino)carbonyl]cyclohexyl-carbamate oxalate monohydrate was also added. The mixture was agitated for 7 hours at 68±2° C. The reaction solution was cooled to 25° C. Afterward, 165 ml of water was added and agitating was performed for 20 minutes. Crystals as products were collected by filtration, washed with water, and air-dried at 50° C. to yield 2.124 g of the title compound (with an equivalent recovery of 89%).

[Experimental Example 1] Synthesis of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide As a start, 0.30 g of tert-butyl (1R,2S,5S)-2-({2-[(5-chloropyridin-2-yl)amino]-2-oxoacetyl}amino)-5-(dimethylaminocarbonyl)cyclohexyl-carbamate as synthesized in Executive Example 1 was weighted and suspended in 6 ml of acetonitrile. 0.21 ml of methanesulfonic acid was added. The mixture was agitated for 2 hours at the room temperature. Then 0.49 ml of triethylamine, 0.164 g of 5-methyl-4,5,6,7-tetrahydro[1,3]thiazolo[5,4-c]pyridin-2-carboxylic acid hydrochloride, 0.117 g of hydroxybenzotriazole monohydrate, and 0.149 g of 1-ethyl-3-(3-dimethylaminopropyl) carbodiimide hydrochloride was added into the mixture under an iced bath. The mixture was then agitated for 16 hours at the room temperature. Afterward, triethylamine and water were added, and the mixture was agitated for 1 hour under an iced bath. Crystals as products were collected by filtration so as to yield 0.317 g of the title compound (with an equivalent recovery of 87%).

[Experimental Example 2] Synthesis of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate As a start, 0.25 g of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)-carbonyl]amino}cyclohexyl)ethanediamide as synthesized in Experimental Example 1 was weighted and dissolved in 5 ml of dichloromethane. Then 0.52 ml of p-toluenesulfonate in ethanol solution (1 mole/L) was added, the mixture was agitated at the room temperature. Than, the solvent was evaporated. 3.9 ml of 15% hydrous ethanol was added into the residue and agitating was performed at 60° C. for dissolving the mixture. The mixture afterward was cooled to the room temperature and agitated for one hour. The deposited crystals were collected by filtration, washed with ethanol, and dried under reduced pressure at room temperature for 2 hours, to yield 0.29 g of the title compound (with an equivalent recovery of 92%).

As demonstrated by Executive Example and Experimental Examples discussed above, the disclosed process allows synthesis of the compound of formula (D) to be achieved by using less toxic organic solvents, such as dimethyl sulfoxide as used for Executive Example 1 as discussed previously, opposite to the traditional approach that uses more toxic organic solvents, such as acetonitrile as described in Comparative Example 1. In addition, the disclosed process provides equivalent recoveries slightly higher than that of Comparative Example 1. Particularly, Experimental Examples 1 and 2 produced the compound of formula (1) and its salt hydrate at high equivalent recoveries. It is thus clear that the process of the present invention is superior to the traditional industrial process and helps to reduce environmental pollution. Therefore, the disclosed process is highly useable as a novel industrial process.

The invention claimed is:
1. A process for producing a compound of formula (D):

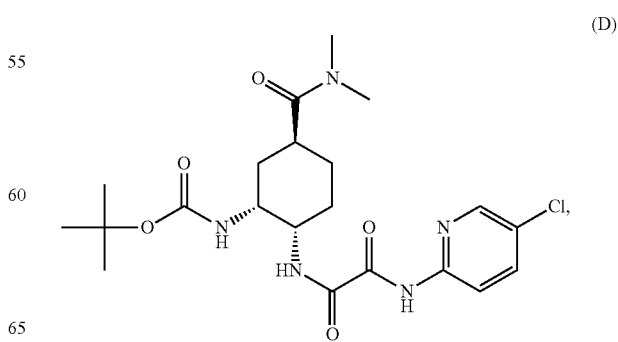

comprising the following steps:

step 1: placing a HCl salt of formula (C) into an organic solvent containing dimethyl sulfoxide or dimethylformamide and treating with a di($C_1$-$C_4$ alkyl)amines:

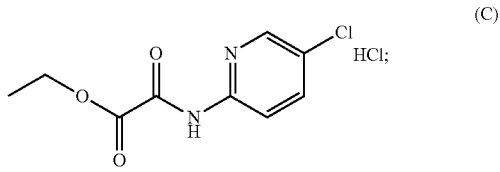

step 2: adding a compound of formula (A) or a salt or a salt hydrate thereof into the mixture of step 1:

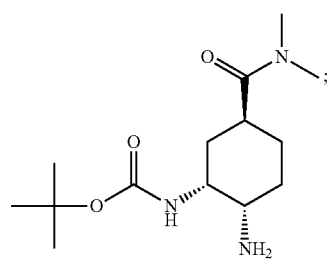

and step 3: crystallizing the mixture processed in step 2.

2. The process of claim 1, wherein the compound of formula (C) is added in an amount of 1.1 to 1.5 molar equivalents with respect to the compound of formula (A).

3. The process of claim 1, wherein the di($C_1$-$C_4$ alkyl)amines comprises diethylamine, dipropylamine, dibutylamine, diisopropylamine or diisobutylamine.

4. The process of claim 1, wherein Step 1 includes adding the compound of formula (C) into the organic solvent first, and then adding the di($C_1$-$C_4$ alkyl)amines.

5. The process of claim 1, wherein Step 1 includes adding the di($C_1$-$C_4$ alkyl)amines into the organic solvent first, and then adding the compound of formula (C).

6. The process of claim 1, wherein said adding of the compound of formula (C) or of the di($C_1$-$C_4$ alkyl)amines is performed at a temperature in the range of 19° C. to 65° C.

7. The process of claim 1, wherein in Step 1, the di($C_1$-$C_4$ alkyl)amines is added in an amount of 1.5 to 5.5 molar equivalents with respect to the compound of formula (C).

8. The process of claim 1, wherein Step 2 includes agitating the mixture at a temperature in the range of 60° C. to 95° C.

9. The process of claim 8, wherein a duration for said agitating is in the range of 4 hours to 24 hours.

* * * * *